(12) United States Patent
Kozloski et al.

(10) Patent No.: US 9,311,360 B2
(45) Date of Patent: Apr. 12, 2016

(54) ASSOCIATION OF DATA TO A BIOLOGICAL SEQUENCE

(71) Applicant: International Business Machines Corporation, Armonk, NY (US)

(72) Inventors: James R. Kozloski, New Fairfield, CT (US); Clifford A. Pickover, Yorktown Heights, NY (US); Jacinta M. Wubben, Victoria (AU); Ruhong Zhou, Fort Lee, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 152 days.

(21) Appl. No.: 13/689,157

(22) Filed: Nov. 29, 2012

(65) Prior Publication Data

US 2014/0089329 A1  Mar. 27, 2014

Related U.S. Application Data

(63) Continuation of application No. 13/628,967, filed on Sep. 27, 2012, now abandoned.

(51) Int. Cl.
   *G06F 17/30* (2006.01)
   *G06F 19/22* (2011.01)

(52) U.S. Cl.
   CPC ............ *G06F 17/3053* (2013.01); *G06F 19/22* (2013.01)

(58) Field of Classification Search
   CPC ..................................................... G06F 19/22
   USPC ........................................... 707/749; 702/19
   See application file for complete search history.

(56) References Cited

U.S. PATENT DOCUMENTS

| | | | | |
|---|---|---|---|---|
| 5,866,363 A | * | 2/1999 | Pieczenik | A61K 38/17 435/320.1 |
| 6,836,733 B1 | * | 12/2004 | Olson | G06F 19/22 702/20 |
| 6,941,317 B1 | * | 9/2005 | Chamberlin | G06F 19/28 435/6.12 |
| 7,039,238 B2 | * | 5/2006 | Sonmez | G06F 19/22 382/219 |
| 7,053,268 B1 | * | 5/2006 | Donaldson | C12N 15/8234 435/252.3 |
| 7,133,780 B2 | * | 11/2006 | Siani-Rose | G06F 19/24 702/19 |

(Continued)

OTHER PUBLICATIONS

Tsaftaris, S. A. et al., "In silico estimation of annealing specificity of query searches in DNA databases," Journal of Japan Society of Simulation Technology (JSST) special issue, "Applicaiton and Simulation of DNA Computing", vol. 24, No. 4, Dec. 2005, pp. 268-276.

*Primary Examiner* — Thu-Nguyet Le
*Assistant Examiner* — Nargis Sultana
(74) *Attorney, Agent, or Firm* — Cantor Colburn LLP; Vazken Alexanian

(57) ABSTRACT

A method for associating data with a target biological sequence includes identifying, in a network, one or more references to data, where the data has a relevance level greater than a predetermined threshold. The method includes associating the one or more references to one or more probe sequences corresponding to a segment of a biological sequence to which the data pertains The one or more probe sequences are ranked based on one or more criteria and the probe sequences are assigned a level of affinity to a segment of the target biological sequence based at least on the ranking of each reference.

17 Claims, 9 Drawing Sheets

(56) References Cited

U.S. PATENT DOCUMENTS

| | | | |
|---|---|---|---|
| 7,133,781 B2* | 11/2006 | Toll | G06F 19/22 702/19 |
| 7,243,112 B2* | 7/2007 | Qu | G06F 19/12 |
| 7,428,527 B2* | 9/2008 | Watanabe | G06F 19/28 |
| 7,650,343 B2* | 1/2010 | Fellenberg | G06F 19/28 707/999.1 |
| 7,979,446 B2* | 7/2011 | Malanoski | G06F 19/22 702/20 |
| 8,150,885 B2* | 4/2012 | Keith, Jr. | G06F 17/30327 707/797 |
| 8,412,462 B1* | 4/2013 | Ganeshalingam | G06F 19/22 702/19 |
| 2002/0183933 A1* | 12/2002 | Webster | C12Q 1/6816 702/19 |
| 2002/0183936 A1* | 12/2002 | Kulp | G06F 19/28 702/19 |
| 2003/0211474 A1* | 11/2003 | Yakhini | C12Q 1/6832 506/9 |
| 2004/0030504 A1* | 2/2004 | Helt | G06F 19/22 702/20 |
| 2004/0236740 A1* | 11/2004 | Cho | G06F 17/30705 |
| 2005/0049795 A1* | 3/2005 | Fikuda | G06F 19/22 702/20 |
| 2005/0131649 A1* | 6/2005 | Larsen | G06F 19/28 702/19 |
| 2006/0136144 A1* | 6/2006 | Kamentsky | C12Q 1/6813 702/20 |
| 2006/0142949 A1* | 6/2006 | Helt | G06F 19/26 702/20 |
| 2007/0168135 A1* | 7/2007 | Agarwal | G06F 19/18 702/19 |
| 2008/0140320 A1* | 6/2008 | Stephens | G06F 19/14 702/20 |
| 2009/0055425 A1* | 2/2009 | Evans | G06F 19/22 |
| 2010/0184609 A1* | 7/2010 | Passetti | G06F 19/22 506/8 |
| 2012/0035857 A1* | 2/2012 | Stenger | C12Q 1/6888 702/19 |
| 2012/0053845 A1* | 3/2012 | Bruestle | G06F 19/18 702/20 |
| 2012/0236861 A1* | 9/2012 | Ganeshalingam | H04L 45/00 370/392 |
| 2013/0198118 A1* | 8/2013 | Kowalczyk | G06N 99/005 706/12 |
| 2013/0218733 A1* | 8/2013 | Rago | H04L 63/08 705/30 |
| 2013/0310260 A1* | 11/2013 | Kim | C12Q 1/6869 506/2 |
| 2014/0058682 A1* | 2/2014 | Nasu | G06F 19/20 702/19 |

* cited by examiner

| TABLE |||
|---|---|---|
| REFERENCE | DATA | PROBE |
| URL1 | DOCUMENT | tgccggaatc |
| URL2 | TOOL | gatgggcccc |
| URN1 | BIOGRAPHICAL INFORMATION | gtcggggaac |
| REFERENCE1 | ORGANIZATION | tgccggaatc |

FIG. 6

SEQUENCE LISTING

<160> NUMBER OF SEQ ID NOS: 7

<210> SEQ ID NO 1
<211> LENGTH: 29
<212> TYPE: DNA
<213> ORGANISM: Homo sapiens

<400> SEQUENCE: 1

-continued

```
tgcggacctc ggagggcccc atccccacc                                    29

<210> SEQ ID NO 2
<211> LENGTH: 30
<212> TYPE: DNA
<213> ORGANISM: Homo sapiens

<400> SEQUENCE: 2
acgcctggag cctcccgggg taggggtgg                                    30

<210> SEQ ID NO 3
<211> LENGTH: 10
<212> TYPE: DNA
<213> ORGANISM: Homo sapiens

<400> SEQUENCE: 3
tgccggaatc                                                         10

<210> SEQ ID NO 4
<211> LENGTH: 10
<212> TYPE: DNA
<213> ORGANISM: Homo sapiens

<400> SEQUENCE: 4
gatgggcccc                                                         10

<210> SEQ ID NO 5
<211> LENGTH: 10
<212> TYPE: DNA
<213> ORGANISM: Homo sapiens

<400> SEQUENCE: 5
gtcggggaac                                                         10

<210> SEQ ID NO 6
<211> LENGTH: 10
<212> TYPE: DNA
<213> ORGANISM: Homo sapiens

<400> SEQUENCE: 6
ggggaaaatt                                                         10

<210> SEQ ID NO 7
<211> LENGTH: 10
<212> TYPE: DNA
<213> ORGANISM: Homo sapiens

<400> SEQUENCE: 7
cccctttaa                                                          10
```

ASSOCIATION OF DATA TO A BIOLOGICAL SEQUENCE

CROSS-REFERENCE TO RELATED APPLICATION

This application is a continuation of U.S. patent application Ser. No. 13/628,967, filed Sep. 27, 2012, the disclosure of which is incorporated by reference herein in its entirety.

BACKGROUND

The present disclosure relates to a simulated binding of data to a biological sequence, and in particular to identifying data that is relevant to a biological sequence, ranking the data according to its importance, and providing the data to a user according to the ranking.

Analysis of biological data, including biological sequences, may require large amounts of data stored on different computers to perform the analysis. Biological data being researched may be annotated by a program to refer to data, such as research publications, related to the biological data. This allows a researcher to see other data that is related to the present research of the biological data. While research articles and other publications are useful for analyzing biological data, other resources are also useful, such as analysis tools and software programs. In addition, over time, the amount of information regarding biological data being resourced grows. When biological data is annotated to refer to related publications, the annotations also increase, which may make it more difficult for a researcher to identify the important information related to present research.

SUMMARY

Exemplary embodiments include a method for associating data with a target biological sequence. The method includes identifying, in a network, one or more references to data, where the data has a relevance level greater than a predetermined threshold. The method includes associating, by a processor, the one or more references to one or more probe sequences corresponding to a segment of a biological sequence to which the data pertains The one or more probe sequences are ranked based on one or more criteria and the probe sequences are assigned a level of affinity to a segment of the target biological sequence based at least on the ranking of each reference.

Embodiments further include a method for simulating annealing with a biological sequence. The method includes identifying a target biological sequence and identifying a plurality of references to data in a network as being relevant references based on a determination that the plurality of references have a relevance level greater than a threshold relevance level. The method further includes associating the relevant references with at least one segment of the target biological sequence. The method further includes ranking the relevant references based on predetermined criteria to determine a level of affinity of the relevant references with the at least one segment of the target biological sequence.

Additional features and advantages are realized by implementation of embodiments of the present disclosure. Other embodiments and aspects of the present disclosure are described in detail herein and are considered a part of the claimed invention. For a better understanding of the embodiments, including advantages and other features, refer to the description and to the drawings.

BRIEF DESCRIPTION OF THE SEVERAL VIEWS OF THE DRAWINGS

The subject matter which is regarded embodiments of the present disclosure is particularly pointed out and distinctly claimed in the claims at the conclusion of the specification. The forgoing and other features, and advantages of the embodiments are apparent from the following detailed description taken in conjunction with the accompanying drawings in which:

FIG. 6 illustrates a table according to embodiments of the disclosure;

DETAILED DESCRIPTION

The large volume of data that may be annotated to a biological sequence may make it difficult for a researcher to identify important data. Embodiments of the present disclosure relate to displaying a simulated annealing of data and references to a biological sequence to allow researchers to quickly identify important information.

Figure 1:
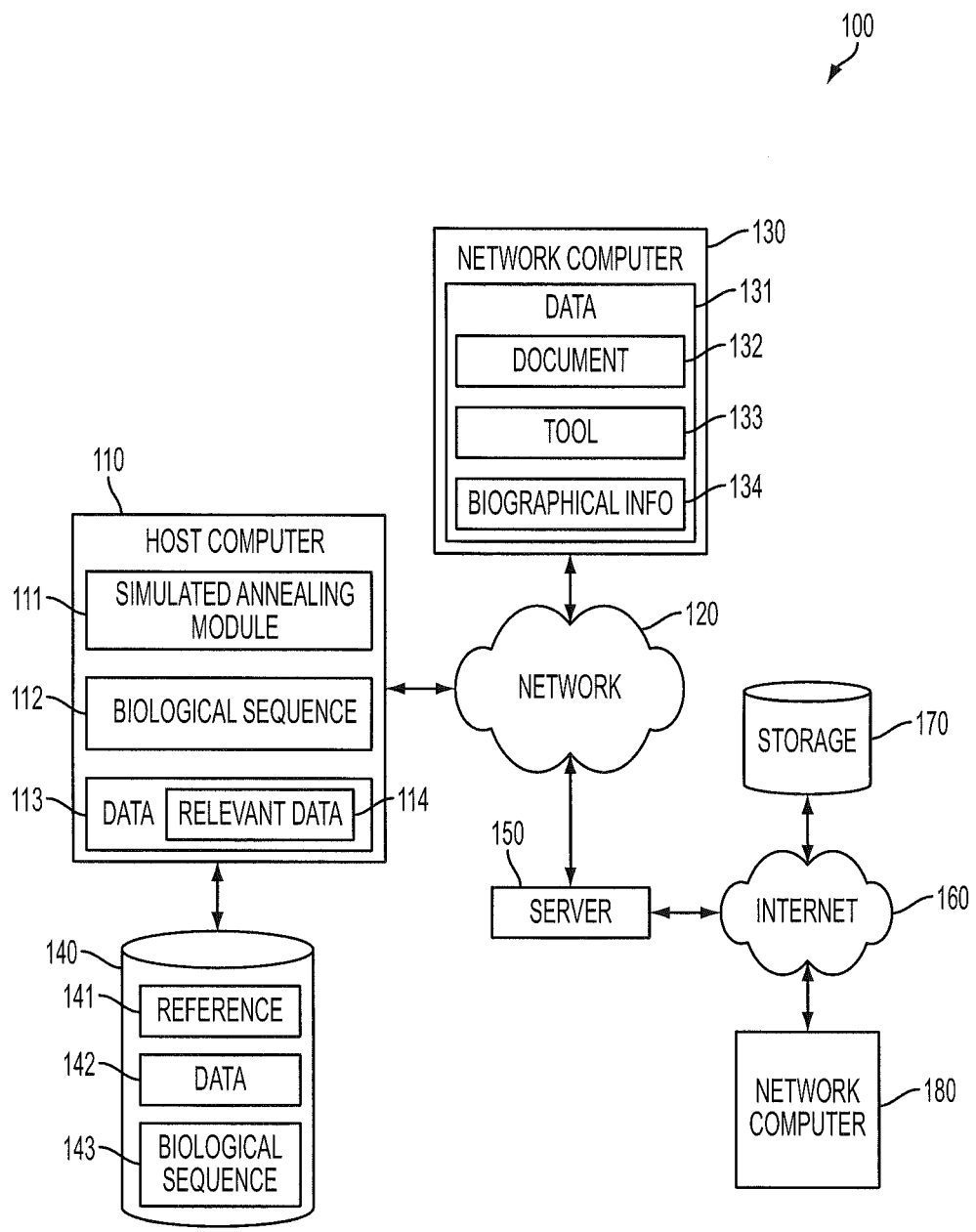
FIG. 1 illustrates a network system according to embodiments of the present disclosure.

FIG. 1 illustrates a network system 100 according to an embodiment of the present disclosure. The system 100 includes a host computer 110 including a simulated annealing module 111, a biological sequence 112 (also referred to as a target biological sequence 112) and data 113. The simulated annealing module 111 is configured to analyze data and references to the data, to determine which data is relevant data 114 to the biological sequence 112, and to determine a level of affinity of the relevant data 114 to the biological sequence 112 based on predetermined ranking criteria. The host computer 110 may display the determined level of affinity by displaying the biological sequence 112, displaying relevant data 114, symbols representing the relevant data 114, or symbols representing references to the relevant data 114, and adjusting a distance of the relevant data 114 (or corresponding symbols) from the biological sequence 112 based on the level of affinity of the relevant data 114 with respect to the biological sequence 112.

The host computer 110 may be connected to a network 120. The network 120 may communicate with one or more network computers 130, which in the present specification and claims refer to computers connected to the network 120 to communicate via the network 120. The network computers 130 may include data 131, such as documents 132, analysis tools 133 and biographical data 134. While only a few types of data are illustrated for purposes of description, any type of data may be stored by the network computers 130. The simulated annealing module 111 may access the data 131 to determine which data 131 is relevant to the biological sequence 112. The simulated annealing module 111 may rank the relevant data 131 based on the predetermined ranking criteria to determine a level of affinity of the data 131 to the biological sequence 112.

The host computer 110 may also be connected to one or more storage devices 140, and the storage devices may store one or more references 141 pointing to data 142, and one or more biological sequences 143 that may be target biological sequences, or biological sequences against which data is compared to determine a level of affinity. For example, the storage 140 may contain a database of biological sequences 143 and a user of the host computer 110 may upload a biological sequence 143 from the storage 140 to the host computer 110 to allow the simulated annealing module 111 to perform an analysis of data, such as data 113, data 131 and data 142 with respect to the biological sequence 143, to determine the level of affinity of the data to the biological sequence 143.

In addition, the network 120 may access one or more of storage 170 and network computers 180 via a server 150 connected to the Internet 160. Alternatively, the host computer 110 may directly connect to the Internet 160. The storage 170 and network computer 180 may include data, references and biological sequences accessible by the host computer 110 to perform analysis.

In embodiments of the present disclosure, the biological sequence 112 or 143 may include any type of biological sequence, including deoxyribonucleic acid (DNA), ribonucleic acid (RNA), an amino acid sequence of a protein, or any other biological sequence. Data includes documents, files, stored biographical information of a person or information of an organization, stored publications, data regarding a number of queries of the simulated annealing module 111 or other systems, data regarding previous analysis performed on the biological sequence 112, analysis tools, algorithms or programs, medical treatments associated with the biological sequence 112, data regarding comments or reviews of publications or tools, or any other data. References include any pointer or address that indicates a location of data or provides additional information regarding the data. Examples include uniform resource locators (URLs), uniform resource names (URNs), hyperlinks, javascript pointers to data, XML pointers to data or any other type of reference to data.

Figure 2:
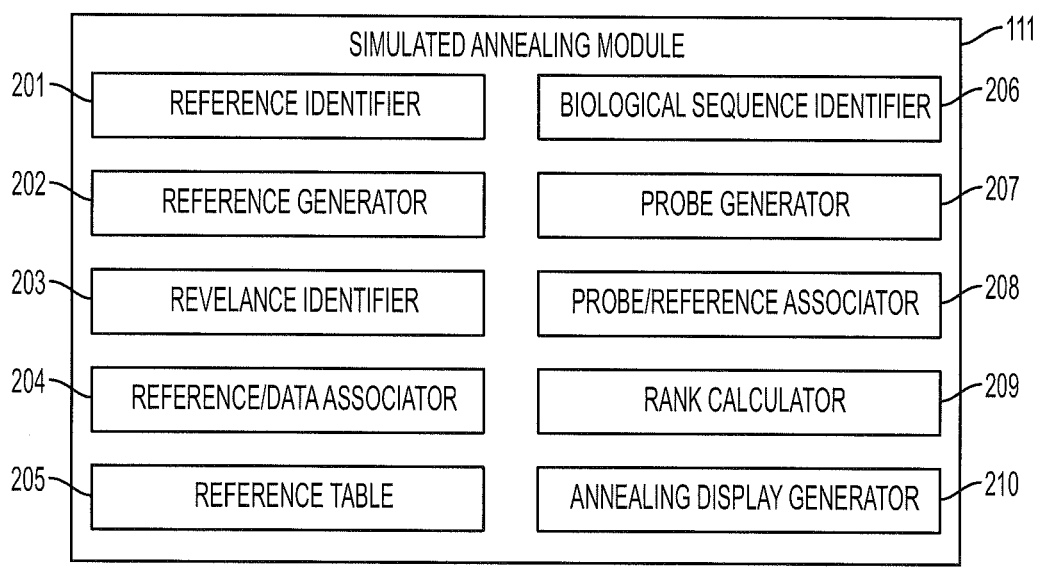
FIG. 2 illustrates a simulated annealing module according to embodiments.

An operation of the host computer 110 including the simulated annealing module 111 will be described below with reference to FIGS. 1 and 2. The simulated annealing module 111 may include a biological sequence identifier 206 to identify a target biological sequence 112. For example, a user accessing the host computer 110 may display the biological sequence 112 or data corresponding to the biological sequence 112 on a display device. Alternatively, the simulated annealing module 111 may automatically, or based on predetermined commands to identify a predetermined biological sequence or a predetermined class or group of biological sequences, search one or more of the host computer 110, storage 140 and 170, and network computers 130 and 180 to identify biological sequences to be target biological sequences 112. In the present specification and claims, a "target biological sequence" is defined as a biological sequence that is selected by a user or program to be subject to ranking of related data, and in some embodiments simulated annealing, as described in embodiments of the disclosure.

The simulated annealing module 111 may include a reference identifier 201, a reference generator 202, a relevance identifier 203 and a reference/data associator 204. The reference identifier 201 may search memory of a device, such as the host computer 110, of connected storage devices 140, of devices 130 connected to a network 120, or of devices 170 and 180 connected to the Internet 160 for references to data, such as URLs that refer to data at a particular location. In addition, in circumstances in which data does not correspond to a reference, or the reference is not in a format usable by the simulated annealing module 111, the reference generator 202 may search memory of a device, such as the host computer 110, of connected storage devices 140, of devices 130 connected to a network 120, or of devices 170 and 180 connected to the Internet 160 for data, such as documents, biographical data, data related to analysis tools, and any other data. The reference generator 202 may then generate a reference, such as a URL that points to a location of the data.

The relevance identifier 203 analyzes the data, such as the data pointed to by the searched references or the data identified by the reference generator 202, to determine whether the data meets a threshold level of relevance. The threshold level of relevance may be based on predetermined criteria, such as a similarity of the data to a target biological sequence, a source of the data, such as an organization supplying the data (e.g. university, company, etc.), an author of the data, a publisher of the data, and a type of operation performed by execution of the data (such as in the case of an analysis tool for analyzing biological sequences). The threshold level of relevance may also be based on a frequency with which the data is accessed or referenced, a frequency with which the data is accessed or referenced by predetermined classes, such as researchers, scientists, professional organizations, etc., or a frequency with which the data is associated with a target biological sequence. In other words, the threshold level of relevance may be related to a target sequence or may include criteria unrelated to the target sequence. The threshold level of relevance may be based on the content of the data, such as an identity of a person or organization that is the subject of biographical information data, or content of a document or file. In addition, the threshold level relevance may be based on usage of the data, such as how often the data is accessed or referenced or by whom the data is accessed or referenced.

Based on a determination that the data meets a threshold level of relevance, the reference/data associator 204 associates a reference, either identified or generated, with the data. For example, the reference and data, or information identifying the data, may be stored in a reference table 205. The probe generator 207 may generate a probe or probe sequence and the probe/reference associator 208 may associate the probe sequence with the reference, such as by adding the probe sequence to the reference table 205. In one embodiment, the probe represents a degree to which the reference, or the data associated with the reference, corresponds to a particular segment of a biological sequence to which the data pertains. The segment of the biological sequence to which the data pertains may be a portion less than the entire biological sequence, but in some examples the segment could correspond to the entire biological sequence. In one embodiment, the probe is identified by a sequence that is complementary to a sequence of a segment of the biological sequence to which the data pertains. For example, if a segment of the biological sequence to which the data pertains has a configuration of "GGGGAAAATT," the probe may correspond to a complementary probe sequence, or "CCCCTTTTAA." Accordingly, the host computer 110 may match references and data to portions of biological sequences pertaining to each reference according to a sequence indicated by a probe sequence. In other embodiments, the probe identifies spatially, numerically or graphically a portion of the biological sequence to which it pertains.

The rank calculator 209 may calculate a rank of each probe sequence, or each reference, or of the data corresponding to each reference and probe sequence. The ranking may be based on one or more criteria, and the criteria may be weighted so that different criteria affect the ranking more than other criteria. For example, a user may set up a profile in the host computer 110 or the simulated annealing module 111, and the user may indicate which indicia the user would prefer to be given the most weight. In one embodiment, the weighting criteria are analogous to biological characteristics of a probe and biological sequence in a biological annealing process.

One criterion, which may be analogous to a biological complementarity requirement, is a determination of a similarity, resemblance, or overlap of the data or the probe with a segment of the target biological sequence. For example, a document may explicitly describe the segment of the target biological sequence or an analysis tool may have been used to analyze the segment of the target biological sequence. Alternatively, a document may describe a similar, but not identical, biological sequence, which may result in a lower ranking.

Another criterion, which may be analogous to a binding affinity of a probe in a biological annealing, is a determination of importance or prestige of a probe, data or reference. The importance of the data may be determined based on information about the data that does not necessarily relate to the target biological information. For example, the importance of the data may be based on one or more of a number of citations the authors of a document have received, the identities of people or organizations that have referenced a document, a university or organization where the data was generated, such as where research was conducted, a type of analysis performed in a document, a name of an author of a document, or any other factors that may provide information regarding the prestige or importance of data in a field. When the data relates to an analysis tool, for example, the importance of the data may be determined based on a type of analysis performed by the tool, a university or organization where the analysis tool was developed, a creator of the analysis tool, or any other factors that may provide information regarding the prestige or importance of the analysis tool.

Another criterion, which may be analogous to probe mobility in a biological annealing, is a determination of a popularity of data. The determination may take into account a frequency with which the data is accesses or cited, such as a frequency with which a document is cited in other publications or a frequency with which an analysis tool is used in a field. In an embodiment in which the data is biographical information, such as information about a researcher, the determination may consider a frequency with which the researcher is cited. In other words, while determining the importance or prestige of the data relates to factors that are not directly associated with the data (such as a prestige of the source of the data), the popularity of the data may relate to the data itself.

Another criterion, which may be analogous to occupancy constraints in a biological annealing, is a determination of a historical applicability of data to a target biological sequence, to the probe or to other probe sequences. For example, the determination may be based on a frequency with which an analysis tool has been used to analyze a target segment of the biological sequence, or a frequency with which a document has been cited in reference to the target segment of the biological sequence.

Although a few examples of ranking criteria have been provided, embodiments of the present disclosure encompass any ranking criteria including prior uses of a tool, prior citations of a document, a quality of citations to the data, affiliations of an author of data, ease-of-use of a tool, cost to implement an analysis tool, number of software or tool citations, a date of citations or references to the data, votes or other determinations of importance of data by crowd sourcing, content of user comments about the data, etc. In addition, in one embodiment a stochastic element may be introduced to the rankings to allow for optimization away from local minima.

In one embodiment, the probe sequence includes or has attached to it the data associated with the ranking criteria. When a target biological sequence is identified, it may be compared with all of the available probe sequences, and the available probe sequences may be ranked based on a similarity with segments of the target biological sequence. Accordingly, in one embodiment, the data and references identified in the system are not directly compared with data associated with the target biological sequence. Instead, a probe sequence having stored therein, attached thereto, or which inherently includes the ranking criteria data is compared to segments of the target biological sequence.

The probe sequences may be generated by systems or users that generated the data and/or references, or the probe sequences may be generated by a system or user that identifies a target biological sequence. For example, in one embodiment, a system that identifies a target biological sequence searches a network for previously-generate probe sequences and performs the ranking operation. In another embodiment, the system that identifies the target biological sequence may search the network, identify relevant data, and generate the probe sequences corresponding to the relevant data. Then the data, references or generated probe sequences may be compared to predetermined criteria and to the target biological sequence. In yet another embodiment, a system may combine both analysis of pre-generated probe sequences with the generation of new probe sequences based on newly-identified data or references in a network.

Once the data, references or probe sequences have been ranked by the rank calculator 209, the annealing display generator 210 generates a graphical display of the ranking. The graphical display may display an icon or other representation of the data, reference, or probe and of the target biological sequence, or one or more target segments of the biological sequence. The annealing display generator may display the ranking by displaying icons associated with data having a higher ranking as being located closer to a corresponding segment of the target biological sequence, while an icon associated with data having a lower ranking are located farther from the segment of the target biological sequence.

In embodiments of the present disclosure, the data may be analyzed by the simulated annealing module 111 to determine relevant data and to rank the data by analyzing one or more of key words in the data, frequency of keywords, groups of key words, frequency of groups of keywords, metadata associated with the data, or any other content of the data or content related to the data.

According to embodiments of the present disclosure, data, references and probe sequences may be competitively ranked to ensure that data, references and probe sequences determined to be of highest interest to a user are more closely associated with a target biological sequence being analyzed by the user.

In one embodiment, in addition to annealing one or more probe sequences to a target biological sequence, the simulated annealing module 111 may anneal one or more probe sequences to one or more other probe sequences. For example, if one probe sequence represents an analysis tool, another probe sequence representing a program or tool for improving the efficiency of the analysis tool may be simulated as being annealed to the first probe sequence. In another example, if a first probe sequence represents a software application, one or more probe sequences representing journal citations including formulas or analysis using the software application may be simulated as being annealed to the first probe sequence.

Figure 3:
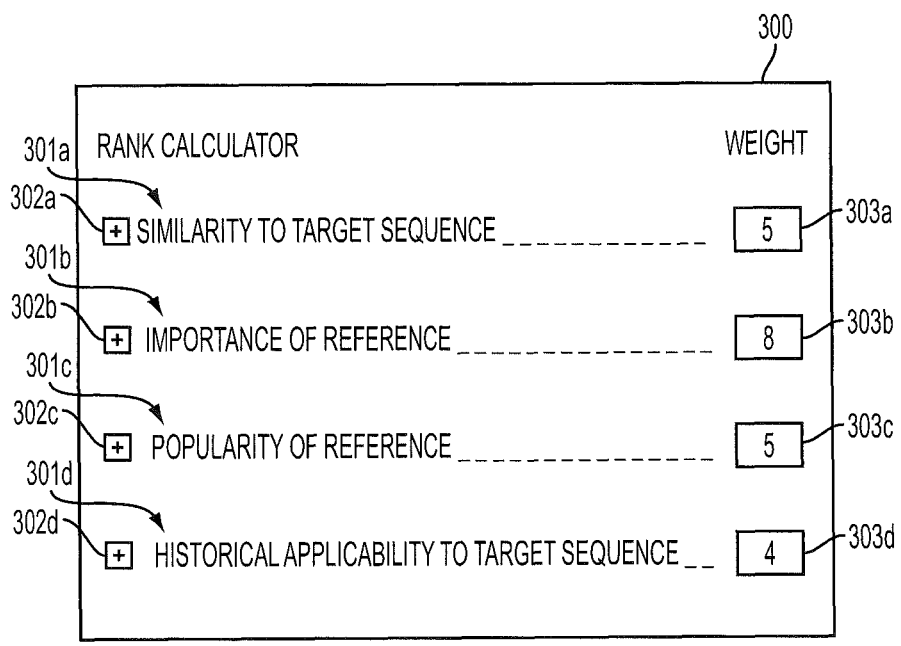
FIG. 3 illustrates a user customization display according to embodiments of the disclosure.

In embodiments of the present disclosure, a user may determine settings, or may generate a profile, to adjust or alter the ranking and display of data, references, and probe sequences. FIG. 3 illustrates a display 300 or graphical user interface (GUI) 300 which may be displayed on an electronic display device, such as a computer monitor, to allow a user to set preferred weights. The display 300 includes rank criteria 301a, 301b, 301c and 301d. In FIG. 3, the rank criteria include "similarity to target sequence" 301a, "importance of reference" 301b, "popularity of reference" 301c, and "historical applicability to target sequence" 301d. However, embodiments of the present disclosure encompass any criteria, including pre-set criteria or criteria generated by a user.

FIG. 3 further illustrates sub-ranking icons 302a to 302d, which may allow a user to further specify ranking preferences. For example, under the sub-ranking icon 302b, a user may specify that in determining an importance of a reference, the organization with which an author or creator is affiliated is more important, and receives a higher weight, than a total number of citations to the author. A user may also set minimum standards, such as a minimum number of citations to data or a reference that is required for the data or reference to obtain any ranking.

The display 300 may further include fields 303a to 303d that are able to be modified by a user to adjust the weighting desired by a user. In one embodiment, the rank calculator 209 utilizes an algorithm to combine a user's selected weight of one or more criteria in combination with information contained within the relevant data or references, or metadata associated with the data or references, to calculate a final ranking of the data, reference, or probe sequence.

Figure 4A:
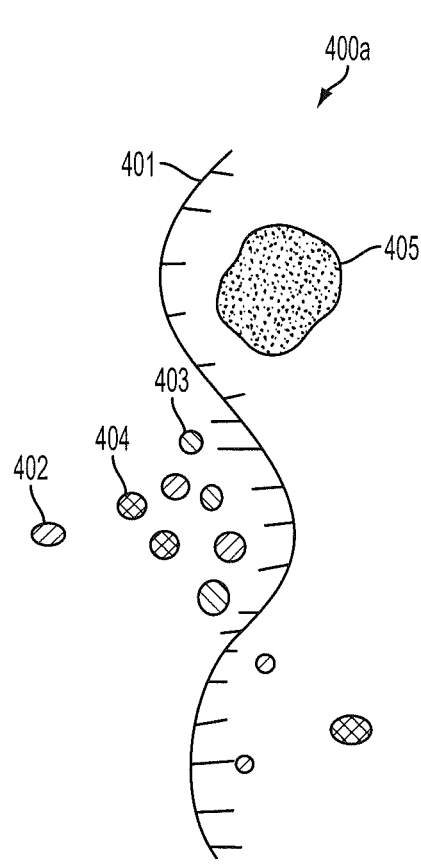
FIG. 4A illustrates an annealing display according to an embodiment of the disclosure.
Figure 4B:
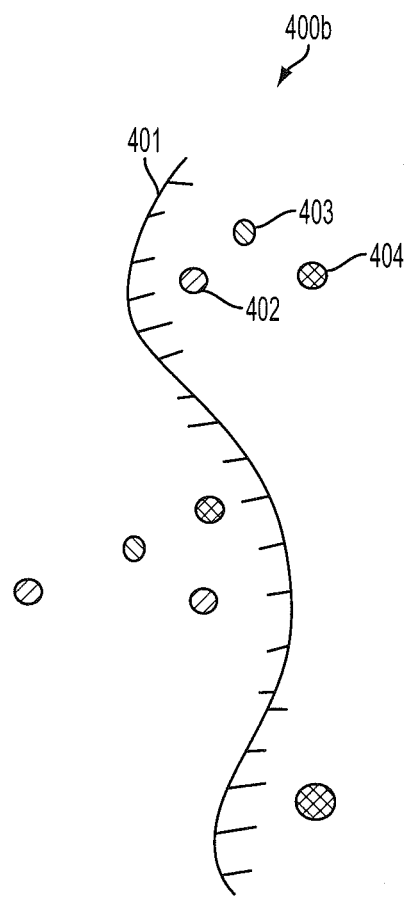
FIG. 4B illustrates an annealing display according to an embodiment of the disclosure.

FIGS. 4A and 4B illustrate displays 400a and 400b of a icons 402, 403 and 404 representing data, references or probe sequences annealing to target biological sequence 401 based on a ranking of the data, references or probe sequences. Alternatively, in addition to annealing to the target biological sequence 401, one or more of the icons 402, 403 and 404 may be annealed to other icons among 402, 403 and 404, representing the annealing of a probe sequence to another probe sequence that is annealed to the target biological sequence 401. Referring to FIG. 4A, icons 402, 403 and 404 having different visual characteristics, such as different cross-hatching, different colors, different shapes or different graphic representations may correspond to different types of data or references. For example, an icon 402 having a first type of cross-hatching may correspond to a document, an icon 403 having a second type of cross-hatching may correspond to an application and an icon 404 having a third type of cross-hatching may correspond to biographical information about a person, such as a researcher. Other types of data that may be represented by the icons 402, 403 and 404 include data about an organization, such as a company or university, computer program information, project information about a research project, information about web pages that may contain relevant information, etc.

The icons are displayed to be vertically (in FIGS. 4A and 4B) aligned with a segment of the target biological sequence 401 according to the probe sequence associated with the data and reference represented by the icons 402, 403 and 404. In addition, the icons are displayed as being a distance away from a segment of the target biological sequence 401 (in a horizontal direction in FIGS. 4A and 4B) based on a ranking of the data or reference associated with the icons. For example, the icons labeled 402 and 404 may be associated with the same or a very similar segment of the biological sequence, as indicated by the close vertical alignment of icons 402 and 404. However, icon 404 may be associated with data having a higher ranking than icon 402, as illustrated by icon 404 being located closer to the target biological sequence than icon 402 in the horizontal direction.

In one embodiment, a user may retrieve the data represented by the icons 402, 403 and 404, or may be provided with information regarding where the data is located, by selecting the icons 402, 403 or 404 with a cursor, touch, or any other user interface. In one embodiment, different ranking characteristics may change an appearance of the icons 402, 403 and 404. For example, an icon representing data that is referenced often may have a larger shape than data that is referenced seldom. An icon representing data that is available by clicking an icon may have a different outline than data that is not. An icon representing a person may have an image of the person. An icon representing a product, such as an analysis tool or program, may have an icon or image associated with the tool or program, such as a trademark.

In one embodiment, if a segment or adjacent segments of the target biological sequence 401 include a relatively large number of icons, the display 400a may generate a blob 405. When a user moves a cursor over the blob 405 or performs any other action for selecting the blob 405, the individual icons may be shown and selected.

FIG. 4B illustrates a display 400b of the same target biological sequence 401 as in FIG. 4A, but the ranking preferences are different corresponding, for example, to preferences selected by a different user. Accordingly, the icons 402, 403 and 404 may be arranged differently and may have different numbers than in FIG. 4A. In embodiments of the present disclosure, a user may modify preferences of the information that the user considers important to personalize information displayed to the user related to a target biological sequence 401.

Figure 5:
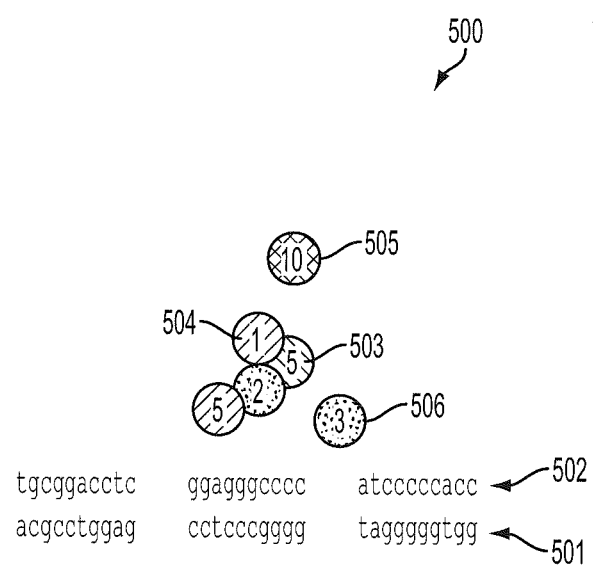
FIG. 5 illustrates an annealing display according to another embodiment of the disclosure.

FIG. 5 illustrates a display 500 according to another embodiment of the present disclosure. In FIG. 5, the target biological sequence 501 is displayed by letters representing, for example, nucleotides, and corresponding probe sequences 502 are represented by complementary letters, or nucleotides that may bond with the nucleotides of the target biological sequence 501. Icons 503, 504, 505 and 506 represent different types of data, such as publications, analysis tools, biographical information, and web page information. The icons 503, 504, 505 and 506 may be located in a horizontal direction (in FIG. 5) based on a segment of the target biological sequence 501 to which the data represented by the icons 503, 504, 505 and 506 is most closely related. The icons 503, 504, 505 and 506 may be separated from the target biological sequence 501 by a distance determined by the ranking of the data or reference associated with the icon 503, 504, 505 and 506.

As illustrated in FIG. 5, the icons 503 to 506 may contain information related to the data that the icon represents. For example, the icons may contain numbers to indicate a number of citations to the data by particular sources. While examples of displays have been provided for purposes of description, embodiments encompass any type of display in which a user may see an importance of data relative to a target biological sequence based on a distance of an icon representing the data from the target biological sequence. In one embodiment, a probe sequence may be further bonded to one or more additional probe sequences. For example, a user may move a cursor over an icon or select the icon, and one or more additional linked icons may appear, corresponding to additional data that is related to the data represented by the selected icon. In one embodiment, the probe sequence may be treated as a target biological sequence, and data may be analyzed and ranked with reference to the probe sequence in the same manner as for the original biological sequence.

FIG. 6 illustrates an example of a table 600 according to an embodiment of the present disclosure. The table 600 may correspond to the reference table 205 of FIG. 2, for example. The table 600 associates a reference, such as a URL, URN, or other address, link or locator, with relevant data and a probe sequence. Examples of relevant data have been discussed previously, and in FIG. 6 the probe sequence corresponds to a biological sequence that is complementary to a segment of a target biological sequence. The table 600 may further include icon information for displaying an icon representing the data or reference, or any other information to be associated with the relevant data and reference. While FIGS. 2 and 6 illustrate tables to associate data, references to the data and probe sequences, embodiments of the present disclosure encompass any data structures for associating data, such as arrays, pointers, or any other types of data structures with which a person or system could associate data with references to the data and with probe sequences.

Figure 7:
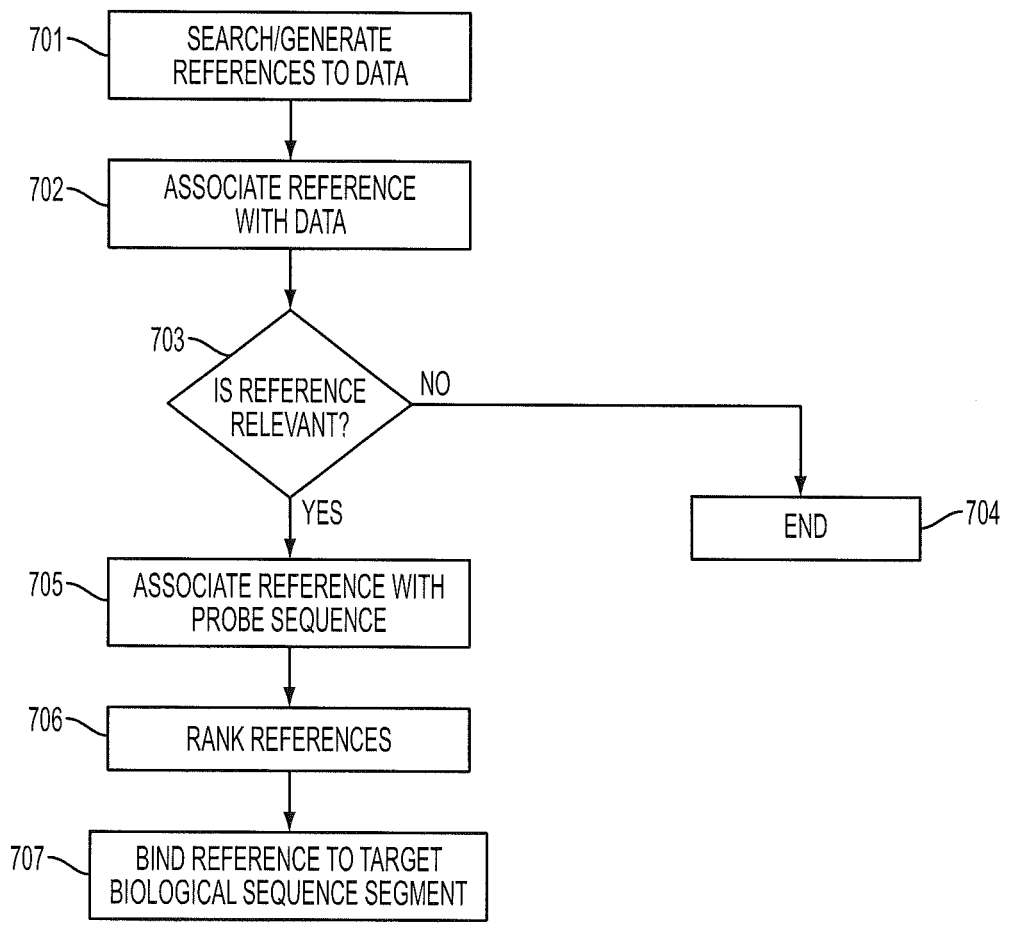
FIG. 7 illustrates a flowchart of a method according to embodiments of the disclosure.

FIG. 7 illustrates a flow diagram of a method according to an embodiment of the present disclosure. In block 701 a reference, such as an address or pointer to data may be found by searching memory in a computer, searching storage devices, searching devices connected to a host device connected to a network, such as the Internet, etc. In addition, references to data found in one or more devices may be generated when no previous reference is found, or when a particular type or format of reference is desired.

In block 702, data is associated with the reference. For example, an entry may be formed in a table or another data structure may be formed to associated with reference with the data to which the reference points. In block 703, it may be determined whether the data is relevant. In other words, a threshold determination of relevance of the data may be made. The threshold level of relevance may be based on predetermined criteria, such as a similarity of the data to a target biological sequence, a source of the data, such as an organization supplying the data (e.g. university, company, etc.), an author of the data, a publisher of the data, and a type of operation performed by execution of the data (such as in the case of an analysis tool for analyzing biological sequences). The threshold level of relevance may also be based on a frequency with which the data is accessed or referenced, a frequency with which the data is accessed or referenced by predetermined classes, such as researchers, scientists, professional organizations, etc., or a frequency with which the data is associated with a target biological sequence. In other words, the threshold level of relevance may be related to a target sequence or may include criteria unrelated to the target sequence. The threshold level of relevance may be based on the content of the data, such as an identity of a person or organization based on stored biographical information, or content of a document or file. In addition, the threshold level relevance may be based on usage of the data, such as how often the data is accessed or referenced or by whom the data is accessed or referenced.

If it is determined in block 703 that the data does not meet the threshold level of relevance, the process with respect to that data ends in block 704. On the other hand, if the data is determined to be sufficiently relevant, the data and reference may be associated with a probe sequence in block 705. The probe sequence may identify at least a portion of a target biological sequence to which the data pertains. In one embodiment, the probe sequence is represented by a complementary sequence to a corresponding segment of the target biological sequence. For example, if the biological sequence is a series of nucleotides, the probe sequence may be a complementary series of nucleotides. In another embodiment, the probe sequence is merely data identifying the portion of the target biological sequence to which the data most closely pertains. In embodiments of the present disclosure, the data may pertain to one segment of the target biological sequence or to more than one segment.

In block 706, the data is ranked based on predetermined criteria to determine an affinity or bond between the data, reference, or probe sequence and a segment of the target biological sequence. The ranking may be based on one or more criteria, and the criteria may be weighted so that different criteria affect the ranking more than other criteria. Examples of ranking criteria include a similarity of the data to the target biological sequence, a relevance of the content of the data to the target biological sequence, an importance or prestige of the data or reference, a popularity of the data or reference, and a historical applicability of the data or reference to target biological sequences.

In one embodiment, a user may add criteria, remove criteria, and adjust a weight of criteria used to rank relevant data, references to the data and probe sequences associated with the data. In embodiments of the present disclosure, different users may generate different profiles or may otherwise indicate different preferences for ranking information related to a target biological sequence. In block 707, the relevant data may be bound to the target biological sequence, or segments of the target biological sequence, based on the ranking. In particular, the target biological sequence may be displayed and icons may be displayed with the target biological sequence representing the data, references and probe sequences.

A graphical display may display an icon or other representation of the data, reference, or probe and of the target biological sequence, or one or more target segments of the biological sequence. The ranking of the data, references or probe sequences may be displayed by displaying icons associated with data having a higher ranking as being located closer to a corresponding segment of the target biological sequence, while icons representing data having a lower ranking are located farther from the segment of the target biological sequence.

Figure 8:
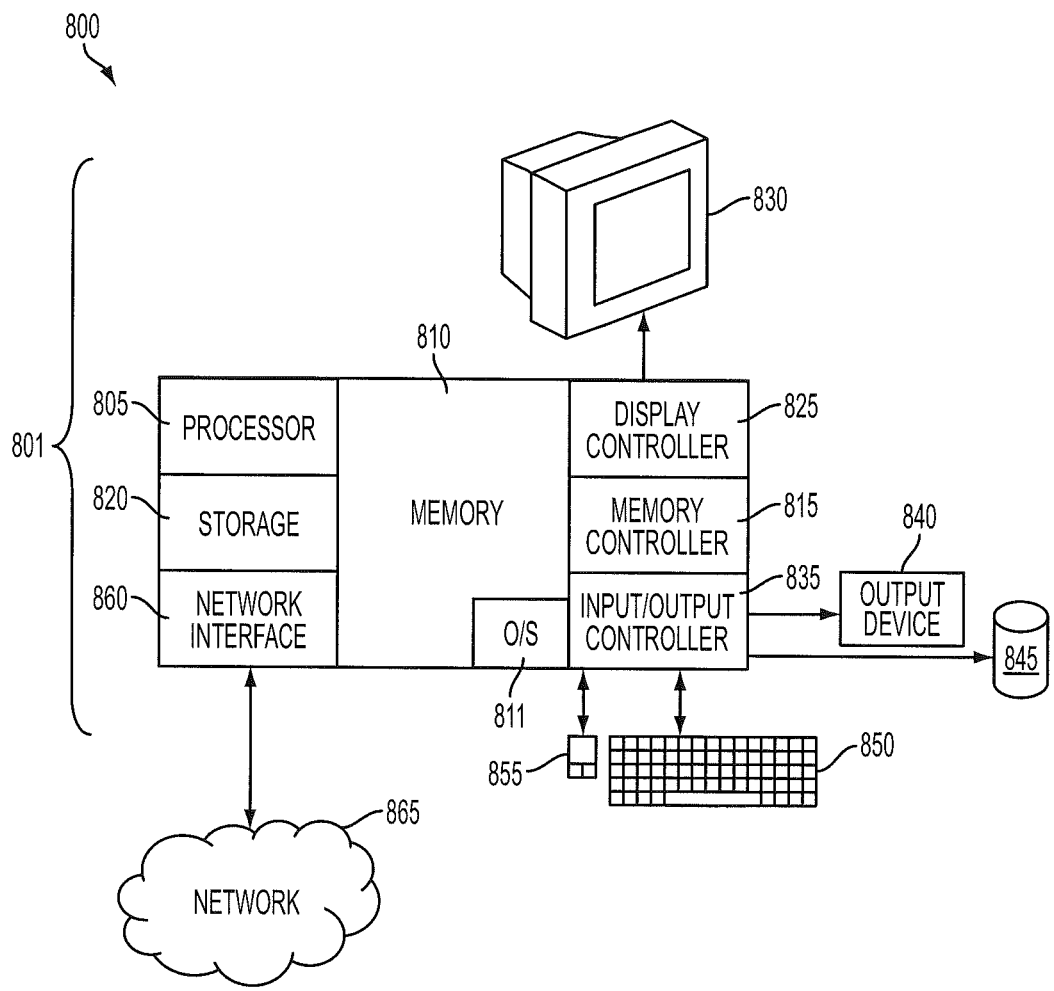
FIG. 8 illustrates a computer system according to embodiments of the disclosure.

FIG. 8 illustrates a block diagram of a computer system 800 according to another embodiment of the present disclosure. The computer 800 may correspond to the host computer 110 of FIG. 1, for example. The methods described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 800 therefore may include general-purpose computer or mainframe 801 capable testing a reliability of a base program by gradually increasing a workload of the base program over time.

In an exemplary embodiment, in terms of hardware architecture, as shown in FIG. 8, the computer 801 includes a one or more processors 805, memory 810 coupled to a memory controller 815, and one or more input and/or output (I/O) devices 840, 845 (or peripherals) that are communicatively coupled via a local input/output controller 835. The input/output controller 835 can be, for example, one or more buses or other wired or wireless connections, as is known in the art. The input/output controller 835 may have additional elements, which are omitted for simplicity in description, such as controllers, buffers (caches), drivers, repeaters, and receivers, to enable communications. Further, the local interface may include address, control, and/or data connections to enable appropriate communications among the aforementioned components. The input/output controller 835 may include a plurality of sub-channels configured to access the output devices 840 and 845. The sub-channels may include, for example, fiber-optic communications ports.

The processor 805 is a hardware device for executing software, particularly that stored in storage 820, such as cache storage, or memory 810. The processor 805 can be any custom made or commercially available processor, a central processing unit (CPU), an auxiliary processor among several processors associated with the computer 801, a semiconductor based microprocessor (in the form of a microchip or chip set), a macroprocessor, or generally any device for executing instructions.

The memory 810 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 810 may incorporate electronic, magnetic, optical, and/or other types of storage media. Note that the memory 810 can have a distributed architecture, where various components are situated remote from one another, but can be accessed by the processor 805.

The instructions in memory 810 may include one or more separate programs, each of which comprises an ordered listing of executable instructions for implementing logical functions. In the example of FIG. 8, the instructions in the memory 810 include a suitable operating system (O/S) 811. The operating system 811 essentially controls the execution of other computer programs and provides scheduling, input-output control, file and data management, memory management, and communication control and related services.

In an exemplary embodiment, a conventional keyboard 850 and mouse 855 can be coupled to the input/output controller 835. Other output devices such as the I/O devices 840, 845 may include input devices, for example but not limited to a printer, a scanner, microphone, and the like. Finally, the I/O devices 840, 845 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 800 can further include a display controller 825 coupled to a display 830. In an exemplary embodiment, the system 800 can further include a network interface 860 for coupling to a network 865. The network 865 can be an IP-based network for communication between the computer 801 and any external server, client and the like via a broadband connection. The network 865 transmits and receives data between the computer 801 and external systems. In an exemplary embodiment, network 865 can be a managed IP network administered by a service provider. The network 865 may be implemented in a wireless fashion, e.g., using wireless protocols and technologies, such as WiFi, WiMax, etc. The network 865 can also be a packet-switched network such as a local area network, wide area network, metropolitan area network, Internet network, or other similar type of network environment. The network 865 may be a fixed wireless network, a wireless local area network (LAN), a wireless wide area network (WAN) a personal area network (PAN), a virtual private network (VPN), intranet or other suitable network system and includes equipment for receiving and transmitting signals.

When the computer 801 is in operation, the processor 805 is configured to execute instructions stored within the memory 810, to communicate data to and from the memory 810, and to generally control operations of the computer 801 pursuant to the instructions.

In an exemplary embodiment, the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In embodiments of the present disclosure, the simulated annealing module 111 may comprise program code stored in the memory 810 and executed by the processor 805. The data and references pointing to the data may be stored in the computer 801 or may be stored on other computers, servers, databases, or other network devices connected to the computer 801 via a network. The simulated annealing module 111 may further include hardware components, such as processors, memory and logic chips or structures for implementing the simulated annealing.

Figure 9:
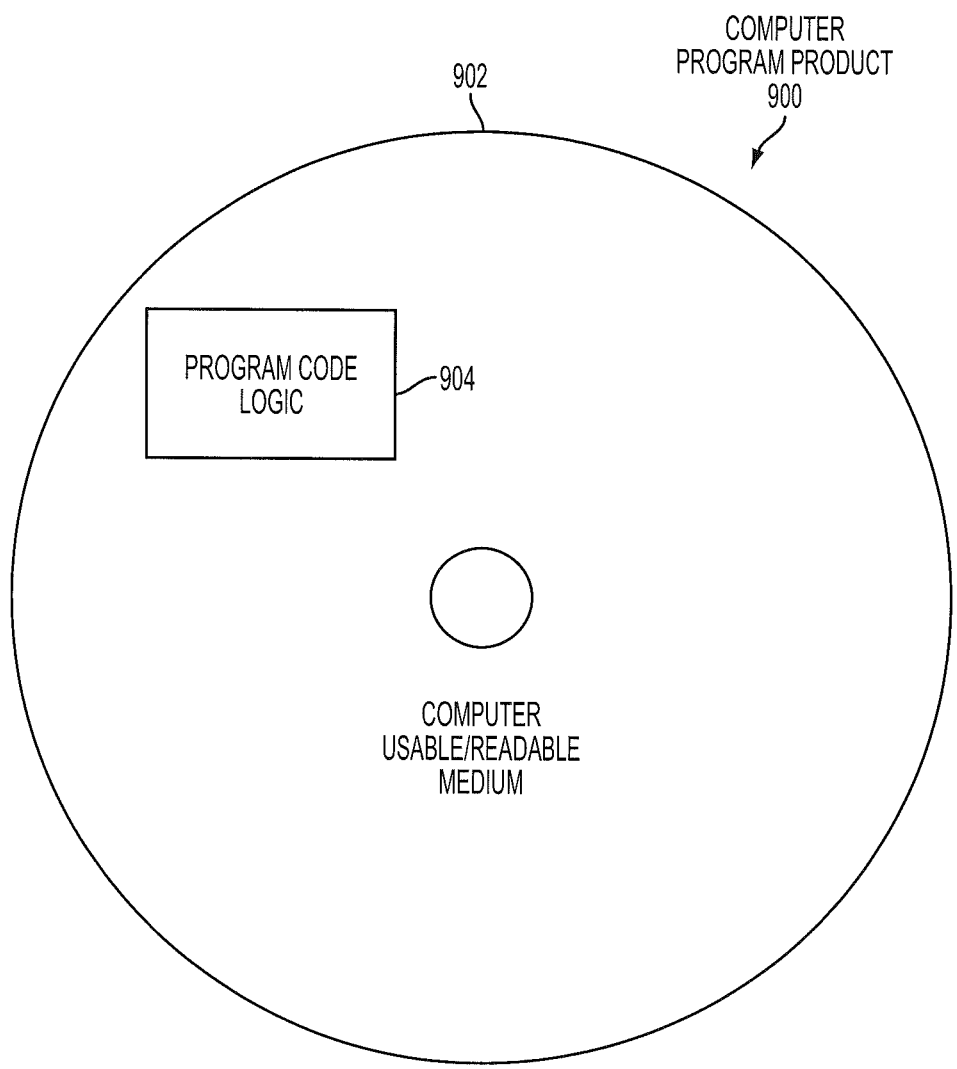
FIG. 9 illustrates a computer program product according to embodiments of the disclosure.

As described above, embodiments can be embodied in the form of computer-implemented processes and apparatuses for practicing those processes. An embodiment may include a computer program product 900 as depicted in FIG. 9 on a computer readable/usable medium 902 with computer program code logic 904 containing instructions embodied in tangible media as an article of manufacture. Exemplary articles of manufacture for computer readable/usable medium 902 may include floppy diskettes, CD-ROMs, hard drives, universal serial bus (USB) flash drives, or any other computer-readable storage medium, wherein, when the computer program code logic 904 is loaded into and executed by a computer, the computer becomes an apparatus for practicing the embodiments. Embodiments include computer program code logic 904, for example, whether stored in a storage medium, loaded into and/or executed by a computer, or transmitted over some transmission medium, such as over electrical wiring or cabling, through fiber optics, or via electromagnetic radiation, wherein, when the computer program code logic 904 is loaded into and executed by a computer, the computer becomes an apparatus for practicing the embodiments. When implemented on a general-purpose microprocessor, the computer program code logic 904 segments configure the microprocessor to create specific logic circuits.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention to the particular embodiments described. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosed embodiments. Many modifications and variations will be apparent to those of ordinary skill in the art without departing from the scope and spirit of the embodiments of the present disclosure.

While embodiments of the present disclosure have been described above, it will be understood that those skilled in the art, both now and in the future, may make various improvements and enhancements which fall within the scope of the claims which follow.

What is claimed is:

1. A method for associating data with a target biological sequence, comprising:

searching one or more storage devices in a network for at least one of a pointer and an address indicating a location of data or providing information regarding the data;

the data comprising at least one of a document, an analysis tool and biological information;

identifying, in the network, one or more pointers or addresses, among the at least one of the pointer and the address, pointing to or addressing data having a relevance level to a biological sequence that is greater than a predetermined threshold;

based on determining that the relevance level of the data is greater than the predetermined threshold, associating, by a processor, each of the at least one pointer and the address to one or more probe sequences corresponding to a segment of the biological sequence to which the data pertains;

associating the one or more probe sequences with at least one of the document, the analysis tool and the biological information;

ranking, by the processor, the one or more probe sequences based on one or more criteria, the ranking of the one or more probe sequences comprising determining a similarity between each probe sequence and the biological sequence to which the pointer or address pertains;

the ranking of the one or more probe sequences further comprising at least one of determining an importance of a source of each pointer or address, determining a popularity of each pointer or address, and determining a historical applicability of each pointer or address to the biological sequence to which the pointer or address pertains;

the determining of the similarity between each pointer or address and the biological sequence to which the pointer or address pertains includes determining a match between each pointer or address a complement of the biological sequence;

the determining of an importance of a source of each pointer or address includes at least one of determining a number of citations of an author of the document, determining an organization to which an author of the document belongs, and determining a type of analysis performed by the analysis tool;

determining a popularity of each reference by at least one of determining a number of citations of the document and a frequency of use of the analysis tool;

determining a historical applicability of each reference to the biological sequence to which the pointer or address pertains by at least one of determining a frequency with which the document has been cited in association with the biological sequence and determining a frequency with which the analysis tool has been used to analyze the biological sequence; and assigning, by the processor, the one or more probe sequences with a level of affinity to a segment of the target biological sequence based at least on the ranking of each pointer or address among the one or more pointers or addresses.

2. The method of claim 1, wherein the one or more pointers or addresses are uniform resource locators (URLs).

3. The method of claim 1, wherein identifying the one or more pointers or addresses having a relevance level greater than a predetermined threshold includes analyzing the one or more pointers or addresses to detect the presence of one or more of key words, phrases, symbols and sources of the one or more pointers or addresses.

4. The method of claim 1, wherein associating each pointer or address to a probe sequence corresponding to a segment of a biological sequence includes
Associating each pointer or address with a biological sequence that is complementary to the segment of the biological sequence to which the data pertains.

5. The method of claim 1, wherein the at least one probe sequence includes two or more probe sequences corresponding to a same segment of the target biological sequence, and
assigning the two or more probe sequences with a level of affinity to the same segment of the target biological sequence includes competitively comparing the two or more probe sequences such that a probe sequence having a higher ranking is assigned a higher level of affinity than a probe sequence having a lower ranking.

6. The method of claim 1, further comprising displaying a graphical representation of the segment of the target biological sequence on a display; and
displaying a graphical representation of the level of affinity of each probe sequence to the segment of the target biological sequence on the display by adjusting a physical distance of a graphical representation of the probe sequence from the graphical representation of the segment based on the level of affinity of the probe sequence.

7. The method of claim 1, further comprising:
associating a first one of the two or more pointers or addresses with a first probe sequence based on the level of affinity to the segment of the biological sequence; and
simulating annealing of a second probe sequence representing data in the network to the first probe sequence based on a determined affinity of the second probe sequence to the first probe sequence.

8. A method for simulating annealing with a biological sequence, comprising:
identifying a target biological sequence;
searching a storage device on the network for at least one of a pointer and an address indicating a location of data or providing information regarding the data;
wherein the data includes an analysis tool relevant to the segment of the biological sequence;
the importance of the source of data referred to by the relevant pointers or addresses being based on at least one of a source of the analysis tool and a type of analysis performed by the analysis tool;
a popularity of data referred to by the relevant pointers or addresses being based on a frequency of use of the analysis tool;
a historical applicability of data referred to by the relevant pointers or addresses being based on a frequency with which an analysis tool has been used to analyze the segment of the target biological sequence;
wherein the data further includes a document relevant to the at least one segment of the target biological sequence;
the importance of the source of data referred to by the relevant pointers or addresses being based on at least one of a number of citations of an author of the document and an organization with which the author of the document is associated;
a popularity of data referred to by the relevant pointers or addresses being based on at least one of a number of citations to the document;
a historical applicability of data referred to by the relevant pointers or addresses being based on a frequency with which the document has been cited in association with the segment of the biological sequence;
identifying, in the network, one or more pointers or addresses, among the at least one of the pointer and the address, pointing to or addressing data having a relevance level to a biological sequence that is greater than a threshold relevance level;
based on determining that the relevance level of the data is greater than the predetermined threshold relevance level, associating the one or more pointers or addresses with at least one segment of the target biological sequence;
ranking the one or more pointers or addresses based on predetermined criteria to determine a level of affinity of the relevant pointers or addresses with the at least one segment of the target biological sequence; and
the ranking of the one or more pointers or addresses based on the predetermined criteria includes ranking the relevant pointers or addresses based on a correspondence between the relevant and the at least one segment of the target biological sequence, and ranking the relevant pointers or addresses based on at least one of an importance of a source of data referred to by the relevant pointers or addresses, a popularity of the data referred to by the relevant pointers or addresses, and a historical applicability of the data referred to by the relevant pointers or addresses to the at least one segment of the target biological sequence.

9. The method of claim 8, wherein identifying the target biological sequence includes identifying a biological sequence selected by a user in a host computer connected to the network.

10. The method of claim 9, wherein the biological sequence is selected by displaying a graphical representation of the biological sequence on a display device.

11. The method of claim 8, wherein identifying the one or more pointers or addresses to data as being relevant includes detecting the presence of one or more of key words, phrases, symbols and sources of the data referred to by the one or more pointers or addresses.

12. The method of claim 8, wherein the pointers or addresses are uniform resource locators (URLs).

13. The method of claim 8, wherein associating the relevant pointers or addresses with at least one segment of the target biological sequence includes associating the relevant pointers or addresses with probe sequences corresponding to the at least one segment of the target biological sequence.

14. The method of claim 13, wherein the probe sequences include a sequence of nucleotides complementary to a sequence of nucleotides of the at least one segment of the target biological sequence.

15. The method of claim 8, further comprising:
    displaying a graphical representation of the at least one segment of the target biological sequence on a display and a graphical representation of the level of affinity of the relevant pointers or addresses to the at least one segment of the target biological sequence on the display by adjusting a physical distance of a graphical representation of the relevant pointers or addresses from the graphical representation of the segment based on the level of affinity of the relevant pointers or addresses.

16. The method of claim 15, wherein the at least one segment of the target biological sequence is displayed as a helix and the graphical representations of the relevant pointers or addresses are located at varying distances from the helix based on varying levels of affinity of the respective relevant pointers or addresses.

17. The method of claim 15, wherein displaying the graphical representation of the at least one segment of the target biological sequence includes displaying a plurality of contiguous segments of the target biological sequence, displaying a plurality of graphical representations of relevant pointers or addresses located at locations along the graphical representation of the plurality of segments based on an association between a respective segment among the plurality of segments and a respective relevant pointers or addresses, and displaying the plurality of graphical representations of relevant pointers or addresses located at different distances from the graphical representation of the plurality of segments of the target biological sequence based on determined affinities of the respective relevant pointers or addresses with the respective plurality of segments of the target biological sequence.

* * * * *